US006743574B1

(12) United States Patent
Wolfinbarger, Jr. et al.

(10) Patent No.: US 6,743,574 B1
(45) Date of Patent: Jun. 1, 2004

(54) PROCESS FOR DEVITALIZING SOFT-TISSUE ENGINEERED MEDICAL IMPLANTS, AND DEVITALIZED SOFT-TISSUE MEDICAL IMPLANTS PRODUCED

(75) Inventors: Lloyd Wolfinbarger, Jr., Norfolk, VA (US); Perry Lange, Virginia Beach, VA (US); Alyce Linhurst, Virginia Beach, VA (US); Eric Moore, Carrolton, VA (US); Barry Nolf, Virginia Beach, VA (US)

(73) Assignee: Lifenet, Virginia Beach, VA (US)

( * ) Notice: Subject to any disclaimer, the term of this patent is extended or adjusted under 35 U.S.C. 154(b) by 140 days.

(21) Appl. No.: 09/660,422

(22) Filed: Sep. 12, 2000

(51) Int. Cl.$^7$ ................................................ A01N 1/00
(52) U.S. Cl. ........................................ 435/1.1; 435/1.2
(58) Field of Search .................................... 435/1.1, 1.2

(56) References Cited

U.S. PATENT DOCUMENTS

| | | | | |
|---|---|---|---|---|
| 4,776,853 | A | 10/1988 | Klement et al. | 8/94.11 |
| 4,801,299 | A | 1/1989 | Brendel et al. | 623/1.47 |
| 5,336,616 | A | 8/1994 | Livesey et al. | 435/395 |
| 5,432,712 | A | 7/1995 | Chan | 382/191 |
| 5,556,379 | A | 9/1996 | Wolfinbarger | 128/898 |
| 5,558,875 | A | 9/1996 | Wang | 424/422 |
| 5,613,982 | A | 3/1997 | Goldstein | 424/423 |
| 5,632,778 | A | 5/1997 | Goldstein | 424/423 |
| 5,820,581 | A | 10/1998 | Wolfinbarger, Jr. | 604/500 |
| 5,843,180 | A | 12/1998 | Jaffe et al. | 128/898 |
| 5,843,181 | A | 12/1998 | Jaffe et al. | 128/898 |
| 5,843,182 | A | 12/1998 | Goldstein | 128/898 |
| 5,855,617 | A | 1/1999 | Orton | 424/474 |
| 5,855,620 | A | 1/1999 | Bishopric et al. | 128/898 |
| 5,863,531 | A | 1/1999 | Naughton et al. | 424/93.7 |
| 5,899,936 | A | 5/1999 | Goldstein | 128/898 |
| 5,916,266 | A | 6/1999 | Yui et al. | 424/423 |
| 5,976,104 | A | 11/1999 | Wolfinbarger, Jr. | 604/500 |
| 5,993,844 | A | 11/1999 | Abraham et al. | 604/500 |
| 5,997,896 | A | 12/1999 | Carr, Jr. et al. | 424/423 |
| 6,024,735 | A | * 2/2000 | Wolfinbarger, Jr. | 604/500 |
| 6,293,970 | B1 | 9/2001 | Wolfinbarger, Jr. | 604/500 |
| 6,312,474 | B1 | 11/2001 | Francis et al. | 623/23.72 |
| 6,371,992 | B1 | 4/2002 | Tanagho et al. | 623/23.72 |
| 6,376,244 | B1 | 4/2002 | Atala | 435/376 |
| 6,416,995 | B1 | 7/2002 | Wolfinbarger | 623/23.61 |
| 6,428,802 | B1 | 8/2002 | Atala | 424/423 |
| 6,432,710 | B1 | 8/2002 | Boss, Jr. et al. | 435/366 |
| 6,432,712 | B1 | * 8/2002 | Wolfinbarger, Jr. | 435/395 |
| 6,448,076 | B2 | 9/2002 | Dennis et al. | 435/325 |
| 6,479,064 | B1 | 11/2002 | Atala | 424/423 |
| 2001/0049138 | A1 | 12/2001 | Dennis et al. | 264/86 |

OTHER PUBLICATIONS

H.–H. Sievers, et al., "Decellularized pulmonary homograft (SynerGraft) for reconstruction of the right ventricular outflow tract: first clinical experience" Z. Kardiol, vol. 92, No. 53, 2003.

Robert Madden, et al., "Decellularized Cadaver Vein Allografts Used for Hemodialysis Access Do Not Cause Allosensitization or Preclude Kidney Transplanation" Journal of Kidney Diseases, vol. 40, No. 6, Dec. 2002, pp. 1240–1243.

P.M. Dohmen, et al., "In Vitro hydrodynamics of a decellularized pulmonary procine valve, compared with a glutarldehyde and polyurethane heart valve" Journal of Artificial Organs, vol. 25, No. 11, 2002, pp. 1089–1094.

B. S. Conklin, et al., "Development and evaluation of a novel decellularized vascular xenograft" Medical Engineering and Physics, vol. 24, 2002, pp. 173–183.

J. Clark, et al., "Decellularized Dermal Grafting in Cleft Palate Repair" Facial Plastic Surg., vol. 5, 2003, pp. 40–44.

Ronald C. Elkins, et al., "Decellularized human Valve Allografts" Society of Thoracic Surgeons, 2001, pp. S428–S432.

Steven Goldstein, et al., "Transpecies Heart Valve Transplant: Advanced Studies of a Bioengineered Xeno–Autograft" Society of Thoracic Surgeons, 2000, pp. 1963–1969.

Pascal M. Dohmen, et al., "Ross Operation with a Tissue–Engineered Heart Valve" Society of Thoracic Surgeons, 2002, pp. 1438–1442.

David W. Courtman, et al., "Biomechanical and ultrastructural comparison of cryopreservation and a novel cellular extraction of porcine aortic valve leaflets" Journal of Biomedical Materials Research, vol. 29, 1995, pp. 1507–1516.

Gregory Wilson, et al., "Acellular Matrix Allograft Small Caliber Vascular Prostheses" Trans. Am. Sog. Artif. Intern. Organs, 1990, vol. XXXVI, pp. M340–M343.

(List continued on next page.)

*Primary Examiner*—Jean C. Witz
(74) *Attorney, Agent, or Firm*—Crowell & Moring LLP (57) ABSTRACT

The invention provides methodologies and apparatus for producing devitalized soft-tissue implants where the implant retains metabolically non-viable and/or reproductively non-viable cells, and preferably retains large molecular weight cytoplasmic proteins, such implants produced both in small quantities and in commercializable quantities. Such soft-tissue implants include vascular graft substitutes. An devitalized graft is produced by subjecting the tissue sample to an induced pressure mediated flow of an extracting solution, optionally followed by inducing a pressure mediated flow of a salt solution, then washing the tissue to produce the devitalized graft. The devitalized grafts produced are uniform and non-immunogenic. The inventive method allows for the production of multiple devitalized soft tissue implants, where processing time is significantly less than prior art processes and the number of implants produced per day is increased over prior art processes. In clinical use, the devitalized grafts produced exhibit significantly improved in long-term durability and function, and enhanced recellularization post-implantation.

65 Claims, 2 Drawing Sheets

OTHER PUBLICATIONS

David W. Courtman, et al., "The Acellular Matrix Vascular Prosthesis: Investigation of its Potential as a Xenograft for Clinical Application" Biomaterial Tissue Interfaces, vol. 10, 1992, pp. 241–246.

David W. Courtman, et al., "Development of a pericardial acellular matrix biomaterial: Biochemical and mechanical effects of cell extraction" Journal of Biomedical Materials Research, vol. 28, 1994, pp. 655–666.

Gregory J. Wilson, et al., "Acellular Matrix: A Biomaterials Approach for Coronary Artery Bypass and Heart Valve Replacement", Society of Thoracic Surgeons, 1995, pp. S353–S358.

Sotiris A. Korrossis, et al., "Tissue Engineering of Cardiac Valve Prostheses II: Biomechanical Characterization of Decellularized Porcine Aortic Heart Valves" Heart Valve Disease, vol. 11, No. 4, Jul. 2002, pp. 463–471.

* cited by examiner

PROCESS FOR DEVITALIZING SOFT-TISSUE ENGINEERED MEDICAL IMPLANTS, AND DEVITALIZED SOFT-TISSUE MEDICAL IMPLANTS PRODUCED

FIELD OF THE INVENTION

The invention is directed toward methodologies and apparatus for use in the preparation of devitalized, i.e. essentially lacking in reproductively viable cells and/or metabolically viable cells, while preferably retaining reproductively non-viable cells and/or metabolically non-viable cells and/or large molecular weight cytoplasmic proteins including actin, soft-tissue implants, in small quantities and commercializable quantities. Such soft-tissue implants include vascular graft substitutes. These implants can be derived from tissue engineered soft tissue devices, tissue products derived from animal or human donors that contain cells, and that contain or are devoid of valve structures useful in directing the flow of fluids through tubular vascular devices, and/or combinations of natural tissue products and tissue engineered soft-tissue products. The invention includes methodologies and apparatus for producing uniform, gently processed, devitalized multiple soft tissue implants, where processing time is significantly reduced and the number of implants produced per day is increased. The devitalized grafts produced are significantly improved in long-term durability and function when used in clinical applications.

BACKGROUND OF THE INVENTION

Numerous types of vascular graft substitutes have been produced in the last four decades. These vascular graft substitutes have included large and small diameter vascular, blood carrying tubular structures, grafts containing valvular structures (vein substitutes, and heart valve substitutes) and lacking valvular structures (artery substitutes). The materials out of which these vascular grafts have been constructed have included man-made polymers, notably Dacron and Teflon in both knitted and woven configurations, and non-man-made polymers, notably tissue engineered blood vessels such as described in U.S. Pat. Nos: 4,539,716, 4,546,500; 4,835,102; and blood vessels derived from animal or human donors such as described in U.S. Pat. Nos. 4,776,853; 5,558,875; 5,855,617; 5,843,181; and 5,843,180.

The prior art processing methods are directed to decellularizing tissue grafts, i.e. removing all cellular elements leaving a tissue matrix free from cellular elements, and are prohibitively time consuming, easily requiring numerous days, for example anywhere from eight to twenty-one days total processing time. Such long processing times result in proteolytic degradation of the matrix structures of the processed tissues. Over the past few decades numerous efforts have been made to manage the large surgical use of vascular prostheses in the treatment of vascular dysfunctions/pathologies. While vascular prostheses are available for clinical use, they have met with limited success due to cellular and immunological complications, and the inability to remain patent and function. These problems are especially pronounced for small diameter prostheses, i.e. less than about 6 mm. Efforts have been directed at removing those aspects of allograft and xenograft vascular prostheses that contribute to immunological "rejection" and these efforts have focused primarily on development of various "decellularization" processes, which processes require unduly burdensome incubation times. In addition the prior art methods involve using volumes of processing solutions which do not lend themselves to the production of large numbers of vascular grafts, which ability to "scale-up" is necessary for economic clinical use.

The inventive process produces devitalized grafts including but not limited to ligaments, tendons, menisci, cartilage, skin, pericardium, dura mater, fascia, small and large intestine, placenta, veins, arteries, and heart valves. The process is advantageous over prior art processes in that processing times and conditions have been optimized and reduced, and the economics of production have been dramatically improved, resulting in large numbers of uniform, non-immunogenic grafts being produced. The grafts produced are non-immunogenic, are substantially free from damage to the matrix, and are substantially free from contamination including for example free from infectious agents.

The invention involves the use of one or more non-denaturing agent, for example N-lauroylsarcosinate, for the treatment of tissues with the dual objective of devitalization and treatment of tissues to enhance recellularization upon implantation.

The invention is directed at a process for producing devitalized soft-tissue implants including vascular grafts, veins, arteries, and heart valves, where processing times and conditions have been optimized to dramatically improve on the economics of production as well as to produce a graft with minimum damage to the matrix structure of the devitalized graft.

SUMMARY OF THE INVENTION

The inventive process is a process for preparing biological material(s) for implantation into a mammalian cardiovascular system, musculoskeletal system, or soft tissue system. The process removes reproductively viable cells and/or metabolically viable cells, while preferably retaining reproductively non-viable cells and/or metabolically non-viable cells and/or large molecular weight cytoplasmic proteins including for example, actin.

The process provides for the production of commercializable quantities of devitalized soft tissue grafts for implantation into mammalian systems by removing reproductively viable cells and/or metabolically viable cells, while preferably retaining reproductively non-viable cells and/or metabolically non-viable cells and/or large molecular weight cytoplasmic proteins, such proteins including actin, forming an devitalized non-soluble matrix, the matrix having as major components collagens, elastins, hyaluronins, and proteoglycans. The devitalized tissue produced can be implanted into a mammalian system and recellularized in vitro, or recellularized in vitro and subsequently implanted into a mammalian system.

An embodiment of the process includes the following steps:

isolating from a suitable donor a desired tissue sample of the biological material;

extracting the tissue with mildly alkaline hypotonic buffered solution of an endonuclease such as Benzonase® (a registered product of Merck KGaA, Darmstadt, Germany) and one or more non-denaturing detergents, preferably one or more anionic non-denaturing detergents;

optionally treating the tissue with a hypotonic buffered salt solution;

optionally treating the tissue with a hypertonic buffered salt solution;

washing the tissue with water, preferably ultrapure water followed by a water solution optionally containing one or more decontaminating agents including for example chlorine dioxide; and storage in a sealed container in a storage solution optionally including isotonic saline, and/or one or more decontaminating agents.

The invention provides a process for preparing an devitalized soft tissue graft for implantation into a mammalian system and/or commercializable quantities of devitalized soft tissue grafts, including extracting a soft tissue sample with an extracting solution including one or more non-denaturing detergents, for example one or more non-denaturing anionic detergents, and one or more endonucleases, to produce extracted tissue; optionally treating the tissue with a hypertonic buffered salt solution to produce a treated tissue; washing the treated tissue with water followed by treating with a water solution of a decontaminating solution including one or more decontaminating agents to produce the devitalized soft tissue graft; and storing the devitalized soft tissue graft in a storage solution optionally comprising one or more decontaminating agents.

The invention provides a process for devitalizing soft tissue grafts without altering the matrix structure of the graft and without inhibiting subsequent recellularization of the soft tissue graft either in vitro, ex vivo, or in vivo.

The invention also provides a process for preparing an devitalized soft tissue graft for implantation into a mammalian system, including inducing a pressure mediated flow of an extracting solution including one or more non-denaturing detergents and one or more endonucleases, through soft tissue, to produce extracted tissue; inducing a pressure mediated flow of a decontaminating solution including one or more decontaminating agents through the treated tissue, to produce the devitalized soft tissue graft; and storing the devitalized soft tissue graft in a storage solution including one or more decontaminating agents.

The invention provides a process where the extracting solution is recirculated through the soft tissue graft.

The invention further provides a process where the treating solution is recirculated through the soft tissue graft.

The invention also provides a process where the decontaminating solution is recirculated through the soft tissue graft.

The invention provides a process for preparing an devitalized soft tissue graft for implantation into a mammalian system, including extracting a soft tissue sample with an extracting solution comprising one or more non-denaturing detergents and one or more endonucleases, to produce extracted tissue; washing said extracted tissue with a decontaminating solution comprising one or more decontaminating agents to produce said devitalized soft tissue graft; and storing said devitalized soft tissue graft in a storage solution wherein a devitalized soft tissue graft retaining large molecular weight proteins is produced.

The invention also provides a devitalization process does not employ a denaturing detergent.

The invention further provides a devitalization process which includes prior to said step of washing, first washing said extracted tissue with water.

The invention provides a process for preparing an devitalized soft tissue graft for implantation into a mammalian system, including first inducing a pressure mediated flow of an extracting solution including one or more non-denaturing detergents and one or more endonucleases, through soft tissue, to produce extracted tissue; inducing a pressure mediated flow of decontaminating solution optionally including one or more decontaminating agents, through said treated tissue; to produce said devitalized soft tissue graft; and storing said devitalized soft tissue graft in a storage solution.

The invention also provides a devitalization process where prior to the step of inducing, inducing a pressure mediated flow of a washing solution through said extracted tissue.

The invention also provides a devitalization process where extracting solution, and/or the decontaminating solution, and/or the washing solution, is recirculated through said soft tissue graft.

The invention provides a devitalization process where the non-denaturing detergent includes one or more detergents selected from the group consisting of: N-lauroylsarcosinate, a polyoxyethylene alcohol, a polyoxyethylene isoalcohol, a polyoxyethylene p-t-octyl phenol, a polyoxyethylene nonyphenol, a polyoxyethylene ester of a fatty acid, and a polyoxyethylene sorbitol ester.

The invention also provides a devitalization process where the decontaminating solution comprises ultrapure, endotoxin-free, water and/or water solutions of one or more decontaminating agents, where the decontaminating agents are non-reactive towards the one or more non-denaturing detergents.

The invention provides a devitalized tissue graft, including a soft tissue sample substantially free from reproductively viable and/or metabolically viable and/or cellular elements produced by the inventive process where recellularization of the devitalized tissue graft in vivo or in vitro, is enhanced.

The invention further provides a devitalized tissue graft, including a soft tissue sample substantially free from reproductively viable and/or metabolically viable and/or cellular elements.

The invention also provides a devitalized soft tissue sample which is a heart valve, and where the devitalized heart valve leaflets maintain normal coaptation.

DETAILED DESCRIPTION OF THE PREFERRED EMBODIMENTS

Definitions. The below definitions serve to provide a clear and consistent understanding of the specification and claims, including the scope to be given such terms.

Non-denaturing Detergent. By the term "non-denaturing detergent" is intended any detergent that does not denature protein and includes for example, one or more detergents selected from the group consisting of: N-lauroylsarcosinate, a polyoxyethylene alcohol, a polyoxyethylene isoalcohol, a polyoxyethylene p-t-octyl phenol, a polyoxyethylene nonyphenol, a polyoxyethylene ester of a fatty acid, and a polyoxyethylene sorbitol ester.

Decontaminating. Agent By the term "decontaminating agent" is intended one or more agents which remove or inactivate/destroy any infectious material potentially present in a biological tissue sample, for example, such agents include but are not limited to one or more of the following: an antibacterial agent; an antiviral agent; an antimycotic agent; an alcohol for example, methyl, ethyl, propyl, isopropyl, butyl, and/or t-butyl; trisodium phosphate; a preservative such as chlorine dioxide, isopropanol, METHYLPARABIN (Croda, Inc.), antimicrobials, antifungal agents, sodium hydroxide; hydrogen peroxide; a detergent, and ultrapure water, where the decontaminating agent or agents do not biologically alter the matrix components of the soft tissue grafts.

Essentially Free From. By the term "Essentially Free From" is intended for the purposes of the present invention, a soft tissue graft where the material removed (for example, cellular elements and infectious materials) from the soft tissue graft is not detectable using detection means known in the art at the time of filing of this application.

Normal Tissue. By the term "normal tissue" is intended for the purposes of the present invention, a particular soft tissue, for example a vein, artery, heart valve, ligament, tendon, fascia, dura mater, pericardium or skin, present in a living animal, including for example a human, a pig, and/or a cow. Tensile properties, as well as other mechanical properties, of a particular devitalized soft tissue graft approximate, that is, are not statistically significantly different from, the tensile properties of that tissue in a living animal.

Devitalized Soft Tissue Graft. Bye the term "devitalized tissue graft" is intended for the purposes of the present invention, soft tissue including but not limited to veins, arteries, heart valves, ligaments, tendons, fascia, dura matter, pericardium, and skin, from any mammalian source, including but not limited to, a human source, porcine source, and a bovine source, where the devitalized graft produced is allogenic or xenogenic to the mammalian recipient, and where the devitalized tissue is essentially free from reproductively and/or metabolically viable cells, for example, a graft devoid of reproductively viable cells could contain metabolically viable cells that are incapable of increasing the numbers of metabolically viable cells through the normal process of meiosis or mitosis; a graft devoid of metabolically viable cells would, for example, be a graft devoid of cells capable of engaging in those metabolic activities essential to the normal function of those cells, i.e. the cells would be metabolically dead, a metabolically dead cell might still be visible in histology sections appearing similar to a metabolically live cell when viewed with the use of a microscope; cellular remnants, including nucleic acids, small molecular weight proteins, lipids, and polysaccharides, while the devitalized tissue retains reproductively non-viable cells and/or metabolically non-viable cells and/or large molecular weight cytoplasmic proteins, such proteins including for example, actin.

Non-viable Cells: By the term "non-viable cells" is intended cells that are metabolically and/or reproductively non-viable. A metabolically non-viable cell is a cell incapable of engaging in those metabolic activities essential to the normal function of that particular cell, i.e. the cells would be metabolically dead, a metabolically dead cell might still be visible in histology sections. A reproductively non-viable cell is a cell that is incapable of increasing its numbers.

Cellular elements: By the term "cellular elements" is intended those components including but not limited to nucleic acids, small molecular weight proteins, lipids, polysaccharides, and large molecular weight cytoplasmic proteins.

Large Molecular Weight Cytoplasmic Proteins: By the term "large molecular weight cytoplasmic proteins" is intended, cellular elements that are proteins having a high molecular weight that are present in the cytoplasm of cells, such proteins preferably including those having a molecular weight of from about 20 Kdaltons to about 2–4 million Kdaltons, and include for example actin, myosin, and/or neurofilaments.

Salt Solution: By the term "salt solution" is intended water solutions of one or more salts. Suitable salts include but are not limited to: sodium hydroxide, sodium phosphate, potassium sulfate, lithium sulfate, calcium phosphate, potassium phosphate, lithium phosphate, ammonium chloride, magnesium chloride, calcium sulfate, calcium chloride, calcium hydroxide, magnesium chloride, lithium chloride, potassium chloride, and sodium chloride.

Storage Solution: By the term "storage solution" is intended a solution for storing the devitalized tissue graft and includes for example isotonic saline and/or a decontaminating solution optionally including one or more decontaminating agents. Such solutions include for example, solutions of chlorine dioxide; alcohol solutions; isotonic solution containing one or more decontaminating agents, the decontaminating agents including for example low concentrations of chlorine dioxide or peracetic acid, 70% alcohol (preferably, for example ethanol or isopropanol), Paragon or Mackstat DM (DMDM Hydantoin & methylparaben, CAS no. mixture HMIS code 210, DMDM Hydantoin CAS no. 6440-58-0, HMIS code 300, respectively; McIntyre Group; Ltd, University Park, Ill., USA), ioding formulations, and/or isotonic saline.

The invention provides a process for removing viable cells, cellular remnants, nucleic acids, small molecular weight proteins, lipids, and polysaccharides, while retaining metabolically non-viable and/or reproductively non-viable cells and/or retaining large molecular weight cytoplasmic proteins including for example, actin, and without resultant damage to the matrix and/or tissue structure. Preferably, the tissue thickness does not exceed about 8 mm, more preferably does not exceed about 6 mm, and most preferably does not exceed about 4 mm, such that the time intervals described herein are sufficient for the process solutions to penetrate the tissue. Processing times can be altered to accommodate thicker tissues. A quantity of endonuclease is used for a given volume of tissue, such that the quantity is sufficient to digest the DNA within that volume of tissue.

The invention recognizes that the mechanical strength of soft tissue graft biomaterials resides in the matrix structure of the graft. The matrix structure of these biomaterials include collagens, elastins, mucopolysaccharides and proteoglycan components. The devitalization process does not compromise the mechanical strength of the graft necessary for in situ function.

Although the description of the invention is directed primarily at processing vascular graft materials, it should be appreciated that this invention is not restricted to processing of vascular graft materials and can also be directed to processing non-vascular soft tissue grafts. Such tissue grafts include, but are not limited to, tissues such as tendons, fascia, ligaments, pericardium, intestine, skin, dura, and cartilage. Such soft tissue can be processed by one of ordinary skill in the art to which the present invention pertains by simple manipulation of the inventive processing times, without undue experimentation.

Tissue is processed according to the invention by surgically removing normal healthy tissues (for example, veins, arteries, heart valves) from animals or humans. The removed tissue is then transported to a processing facility where the tissue is cleaned of extraneous matter and quickly submersed in the first processing (extracting) solution which includes hypotonic buffered solutions containing one or more endonucleases, for example Benzonase®, and one or more non-denaturing detergents including for example, N-lauroylsarcosinate. Other suitable non-denaturing detergents include N-lauroylsarcosinate, a polyoxyethylene alcohol, a polyoxyethylene isoalcohol, a polyoxyethylene p-t-octyl phenol, a polyoxyethylene nonyphenol, a polyoxyethylene ester of a fatty acid, and a polyoxyethylene sorbitol ester. Procurement and transport of tissue is preferably carried out sterilely and is held in a sterile container on wet ice in a solution iso-osmolar to the cellular population of the tissue being procured and transported. Furthermore, antibiotics may be added to the procurement and transport solution. The invention includes the use of one or more decontaminating agents including for example one or more antibiotics, anti-fungal agents or anti-mycotic agents. Other such agents can be added during processing if so desired to maintain sterility of the procured tissues.

According to an aspect of the invention, a process for preparing biological material for implantation into a mammalian cardiovascular system, musculoskeletal system, or soft tissue system, or for recellularization in vitro, is provided and includes removing cells, cellular remnants, nucleic acids, small molecular weight proteins, lipids, and polysaccharides, while retaining large molecular weight cytoplasmic components, and forms an extrcellular matrix including collagens, elastins, proteoglycans, mucopolysaccharides, and large molecular weight cytoplasmic proteins, the process includes, isolating from a suitable donor a desired tissue sample of the biological material, extracting the tissue with mildly alkaline hypotonic buffered solution of one or more endonucleases, for example Benzonase®, and one or more non-denaturing detergents including for example, N-lauroylsarcosinate. Other suitable non-denaturing detergents include N-lauroylsarcosinate, a polyoxyethylene alcohol, a polyoxyethylene isoalcohol, a polyoxyethylene p-t-octyl phenol, a polyoxyethylene nonyphenol, a polyoxyethylene ester of a fatty acid, and a polyoxyethylene sorbitol ester. Thereafter, the tissue is optionally washed with a hypotonic buffered salt solutions, optionally followed by washing with a hypertonic salt solution. Thereafter, the tissue is washed with water, and optionally followed by a wash of water optionally containing one or more decontaminating agents, such decontaminating agents including for example, chlorine dioxide, and alcohol. The decontaminated devitalized tissue produced is then stored in a storage solution in a sealed container, the storage solution optionally containing one or more decontaminating agents, such solutions including for example, isotonic saline; solutions of chlorine dioxide; alcohol solutions; isotonic solution containing one or more decontaminating agents, the decontaminating agents including for example low concentrations of chlorine dioxide or 70% isopropanol.

The invention provides for the removal of cellular components without resultant damage to the matrix structure in which the cells resided, while ensuring that the repopulation enhancing large molecular weigh cytoplasmic proteins, including cytoskeletal proteins including for example, actin, are retained.

Preferably, the soft tissue sample thickness does not exceed about 4 mm such that the time intervals described herein are sufficient for the solutions to penetrate the tissue. The concentration of endonuclease utilized is based on calculations designed at achieving a sufficient quantity of endonuclease within a given volume of tissue which is sufficient to digest the DNA within that volume of tissue and is not arbitrarily chosen based on volume of processing solution. The inventive process maintains the mechanical strength of the soft tissue graft biomaterials in part because the process does not detrimentally affect the matrix structure of the graft.

The invention provides for the production of soft tissue grafts, which are readily repopulated by recipient cells, post implantation, or readily repopulated in vitro. The inventors surprisingly discovered producing a devitalized tissue which retains large molecular weight cytoplasmic proteins results in enhanced repopulation of the devitalized tissue graft post implantation.

The inventors further discovered that the use of low salt concentrations in the tissues prior to or following treatment/extraction with a non-denaturing detergent results in essentially no residual detergent remaining in the tissue, and that this substantially complete removal of detergent also enhances repopulation, post implantation.

Although the description of this invention is directed primarily at processing vascular graft materials, it should be appreciated that this invention can also be directed to processing non-vascular soft tissue grafts such as tendons, fascia, ligaments, pericardium, skin, dura, and cartilage by simple manipulation of processing times and parameters, such manipulation can be readily determined and employed by one of ordinary skill in the art, without undue experimentation.

In the inventive process, normal healthy vessels (veins, arteries, heart valves, tendons, ligaments, fascia, pericardium, intestine, urethra, etc.) are surgically removed from animals or humans, transported to the processing facility where they are cleaned of extraneous matter and immediately submersed in an extracting solution which contains a hypotonic buffered solution containing one or more endonucleases including for example, Benzonase, and one or more non-denaturing detergents including for example, N-lauroylsarcosinate. In that most such vessels are procured at sites distant from the processing facility and that such vessels may ultimately either be cryopreserved or made devitalized, procurement and transport will normally be in a sterile container on wet ice in a solution iso-osmolar to the cellular population of the tissue being procured and transported. Furthermore, antibiotics are preferably added to the procurement and transport solution. One or more decontaminating agents, including for example, one or more antibiotics, can be optionally employed in any step of the inventive process, to maintain sterility of the procured tissues.

Figure 1:
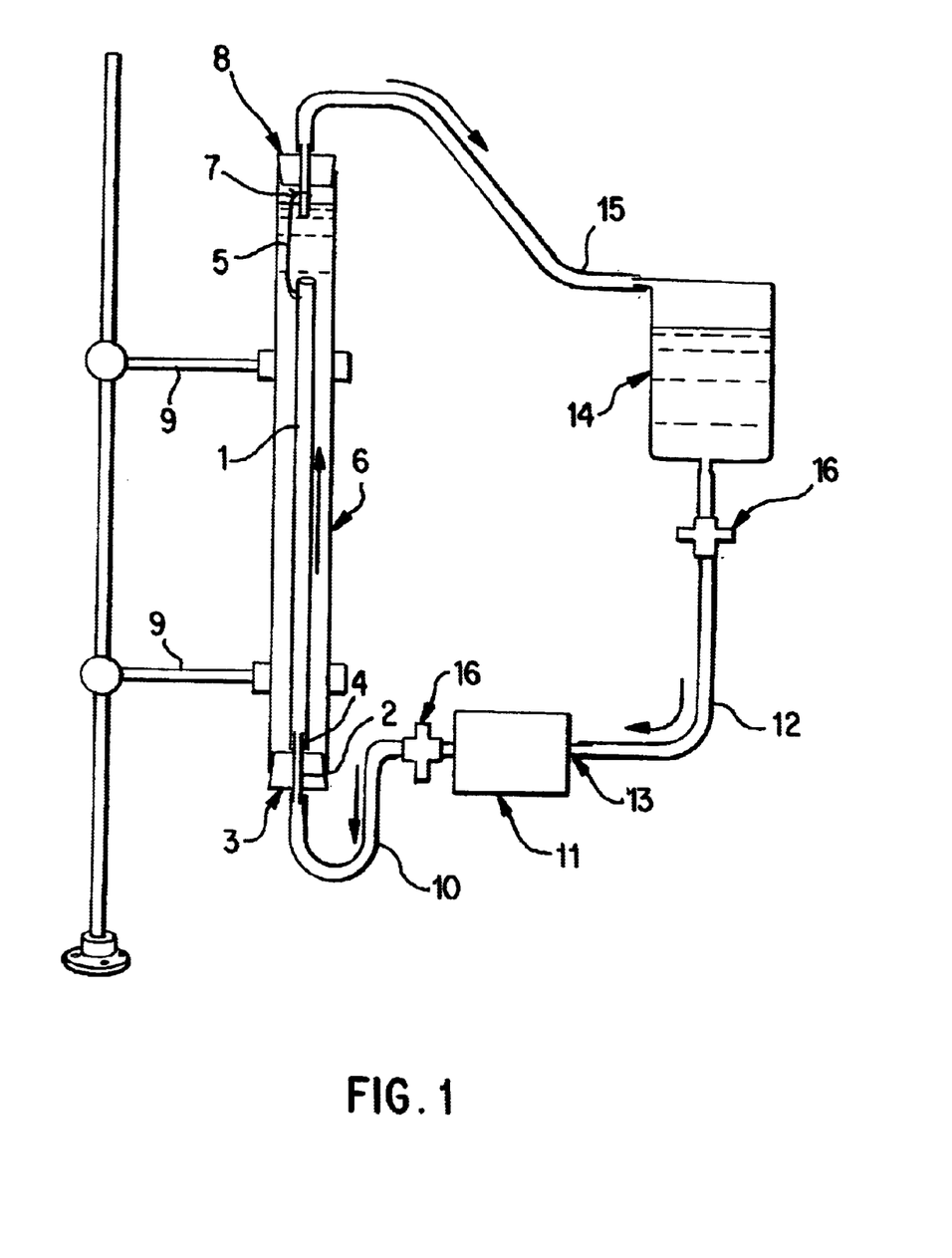
FIG. 1 illustrates a view of one embodiment of the processing chamber showing flow mediated processing of long vein segments.

FIG. 1 illustrates the processing of a long vein grafts (1), the distal end of the vein is cannulated onto the ribbed attachment (2) of the inlet port (3) and a single suture (4) is used to secure the vein. An additional suture line (5) is attached to the proximal end of the vein for later use in maintaining the vein in an extended state in the processing vessel (6). The vein (1) is then removed from the extracting solution and transferred to the processing vessel (6) that has been temporarily inverted. The second suture line (5) along with the vein (1) is passed through the processing vessel (6) and secured to a point (7) on the outlet port end (8) of the processing vessel (6). Prior to closing the processing vessel, a portion of the extracting solution is gently added to the processing vessel and the inlet port (3), with attached vein (1), is then secured. The processing vessel (6) is turned such that the inlet port (3) is down and the outlet port (8) is up and the vessel (6) is attached to its support racking system via clamps (9). Sterile disposable tubing (10) is attached to the inlet port (3) and to pump tubing in a peristaltic pump (11). Further, sterile disposable tubing (12) is attached to the inflow side (13) of the peristaltic pump (11) and to the solution reservoir (14) which will contain all remaining extracting solution. Finally, sterile disposable tubing (15) is attached between the top (outlet) port (8) of the processing vessel (6) and the solution reservoir (14). Sterile, in-line, filters (16) can optionally be added at appropriate positions in the fluid flow to safeguard sterility during processing. The extracting solution is pumped into, through and out of the processing vessel (6) such that flow of fluids through the luminal part of the vein tubule passes into the processing vessel (6) to affect constant solution change in the processing vessel and out through the outlet port (8) to a solution reservoir (14). By processing the vein in an inverted state, air which may be trapped in the luminal space of the vein will be induced to exit facilitating equal access of the processing solutions to the vein tissue being processed. Processing of the vein tissue with the extracting solution is preferably carried out at temperatures ranging from about 4° C. to about 42° C., preferably from about 20° C. to about 37° C., and most preferably from about 20° C. to about 27° C., for time periods ranging from about 1 hour to about 24 hours (overnight as necessary to accommodate processing scheduling of processing staff), preferably from about 6 hours to about 24 hours, and more preferably from about 12 hours to about 24 hours. The extracting solution is preferably pumped at a flow rate of from about 2 mls/min to about 200 mls/min, more preferably from about 5 mls/min to about 100 mls/min and most preferablly from about 30 mls/min to about 60 mls/min. The endonuclease (Benzonase) is optimally active between pH 6 and 10, and from 0° C. to above 42° C. (Merck literature describing product) when provided with 1–2 mM $Mg^{+2}$. Following processing with the extracting solution, the extracting solution can optionally be replaced with: a hypotonic salt solution; a hypotonic salt solution optionally followed by a hypertonic buffered salt solution; or a hypertonic salt solution; followed by processing with water. Thereafter, the tissue is processed with a decontaminating water solution optionally containing one or more decontaminating agents including for example, chlorine dioxide. Under the optional processing procedures, only sufficient solution need be circulated through the processing vessel to affect one volume change of solution in the processing vessel. Under the processing procedures with the hypertonic salt solution or with water, these solutions should be circulated through the tissue at a temperature of from 0° C. to about 42° C., preferably from about 20° C. to about 37° C., and most preferably from about 20° C. to about 27° C., for a time period of at least 3 hours, preferably from about 1 to about 24 hours, and most preferably from about 3 to about 6 hours.

Following processing with the final processing solution, i.e. water or decontaminatingg water solution, sterile isotonic saline is circulated through the tissue such that the available volume of washing solution approximates a 1000-fold dilution of previous solutions. In this final processing step, the vein is removed from the processing vessel and transferred into storage solution, for example, 70% isopropanol, or 0.001% to 0.005% chlorine dioxide in sterile ultrapure water/isotonic saline, and packaged in a volume of storage solution sufficient to cover the tissue preventing dehydration. This packaged graft may then be terminally sterilized, for example using gamma irradiation, if so desired. Artery segments can be similarly processed, taking into consideration that veins have valves and arteries do not, and that veins generally have a smaller internal diameter than arteries, thus dictating slower flow rates with veins.

Figure 2:
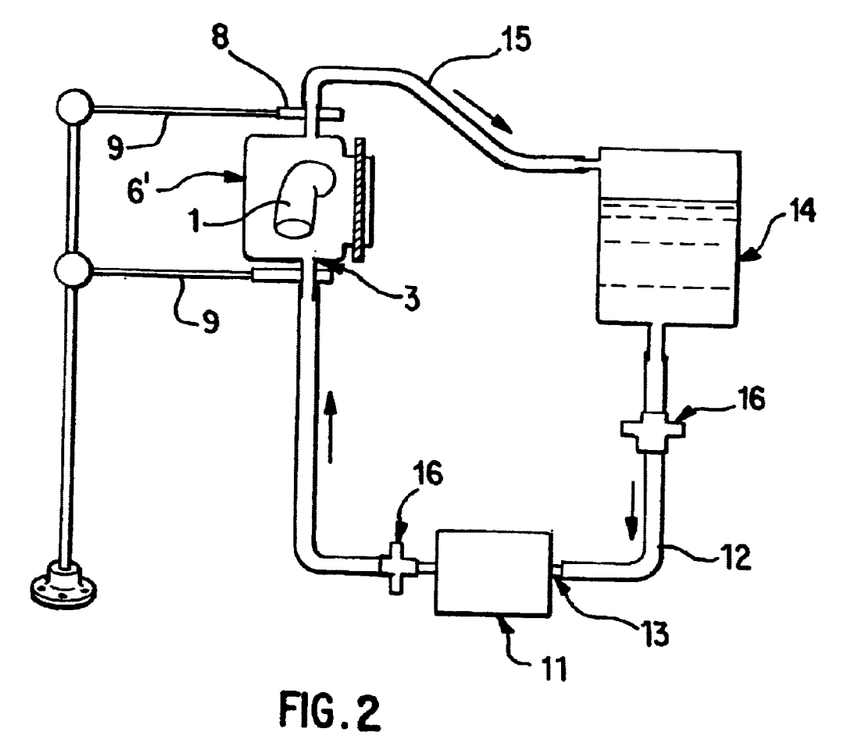
FIG. 2 illustrates a view of an embodiment of the processing chamber showing flow mediated processing of a heart valve.

FIG. 2 illustrates processing heart valve grafts. The heart valve (1) is placed into the deformable processing device (6') such that the valved end of the conduit is directed towards the inlet port (3) and the non-valved end of the conduit is directed towards the outlet port (8). Prior to closing the processing vessel (6'), a portion of the extracting solution is gently added to the processing vessel. The processing vessel (6') is turned such that the inlet port (3) is down and the outlet port (8) is up to effect removal of air bubbles, and the vessel (6') attached to its support racking system via clamps (9). Sterile disposable tubing (10) is attached to the inlet port (3)and to pump tubing in a peristaltic pump (11). Further, sterile disposable tubing (12) is attached to the inflow side (13) of the peristaltic pump (11) and to the solution reservoir (14) which will contain all remaining extracting solution. Finally, sterile disposable tubing (15) is attached between the top (outlet) port (8) of the processing vessel (6') and the solution reservoir (14). Sterile, in-line, filters (16) can optionally be added at appropriate positions in the fluid flow to safeguard sterility during processing. The extracting solution is pumped into, through and out of the processing vessel (6') such that the flow of fluids through the luminal part of the heart valve (1) passes into the processing vessel (6') to affect constant solution change in the processing vessel (6') and out through the outlet port (8) to a solution reservoir (14). By processing the heart valve (1) in this orientation, air which may be trapped in the luminal space of the valve will be induced to exit facilitating equal access of the processing solutions to the valve tissue being processed. Processing of the heart valve (1) tissue with the extracting solution is performed at for example, a temperature of from about 4° C. to about 42° C., preferably from about 20° C. to about 37° C., and most preferably from about 20° C. to about 27° C., for time periods ranging from about 1 hour to about 24 hours (overnight as necessary to accommodate processing scheduling of processing staff), preferably from about 6 hours to about 24 hours, and more preferably from about 12 hours to about 24 hours. The extracting solution is preferably pumped at a flow rate of from about 2 mls/min to about 200 mls/min, more preferably from about 5 mls/min to about 100 mls/min and most preferably from about 30 mls/min to about 60 mls/min. The endonuclease (Benzonase) is optimally active between pH 6 and 10, and from 0° C. to above 42° C. (Merck literature describing product) when provided with 1–2 mM $Mg^{+2}$. Following processing with the extracting solution, the extracting solution is optionally replaced with: a hypotonic salt solution; a hypotonic salt solution optionally followed by a hypertonic buffered salt solution; or a hypertonic salt solution; followed by processing with water. Thereafter, the tissue is processed with a decontaminating water solution optionally containing one or more decontaminating agents including for example, chlorine dioxide. Under the optional processing procedures, only sufficient solution (including the hypertonic salt solution) need be circulated through the processing vessel to affect one volume change of solution in the processing vessel. Under the processing procedures with water and/or disinfectant solutions, these solutions should be circulated through the tissue at a temperature of from 0° C. to about 42° C., preferably from about 20° C. to about 37° C., and most preferably from about 20° C. to about 27° C., for a time period of at least 3 hours, preferably from about 1 to about 24 hours, and most preferably from about 3 to about 6 hours.

Following processing with the final processing solution, i.e. water or decontaminating water solution, sterile isotonic saline is circulated through the tissue such that the available volume of washing solution approximates a 1000-fold dilution of previous solutions. In this final processing step, the heart valve is removed from the processing vessel and transferred into storage solution, for example, 70% isopropanol, or 0.001% to 0.005% chlorine dioxide in sterile ultrapure water/isotonic saline, and packaged in a volume of storage solution sufficient to cover the tissue preventing dehydration. This packaged graft may then be terminally sterilized, for example using gamma irradiation, if so desired.

For all other soft tissue grafts, the tissue is placed into the deformable processing device such that the smaller portion is directed towards the inlet port and the larger (bulkier) end of the tissue is directed towards the outlet port. Preferably the thickness of other soft tissue grafts does not exceed about 8 mm, more preferable does not exceed 5 mm, and most preferably the thickness does not exceed about 2–3 mm. If the thickness of the tissue graft exceeds about 5 mm, incubation and processing times need to be appropriately extended. Such incubation and processing times can be readily selected and employed by one of ordinary skill in the art to which the present invention pertains based on the thickness of the tissue being processed, the type of tissue being processed, and the volume of tissue being processed, without undue experimentation. Prior to closing the processing vessel, a portion of the extracting solution is gently added to the processing vessel. The processing vessel is then turned such that the inlet port is down and the outlet port is up and the vessel is attached to its support racking system for example, via clamps. Sterile disposable tubing is attached to the inlet port and to pump tubing in a peristaltic pump. Further, sterile disposable tubing is attached to the inflow side of the peristaltic pump and to the solution reservoir which will contain all remaining extracting solution. Finally, sterile disposable tubing is attached between the top (outlet) port of the processing vessel and the solution reservoir. Sterile, in-line, filters can optionally be added at appropriate positions in the fluid flow to safeguard sterility during processing. The extracting solution is pumped into, through and out of the processing vessel such that flow of fluids occurs in close proximity to the surfaces of the soft tissue grafts into the processing vessel to affect constant solution change in the processing vessel and out through the outlet port to a solution reservoir. By processing the soft tissue graft in this orientation, the bulkier portions of the soft tissue graft will receive the greatest flow of fluids across the surfaces facilitating equal access of the processing solutions to the tissue being processed. Processing of the soft tissue graft with the extracting solution is preferably performed at a temperature of from about 4° C. to about 42° C., preferably from about 20° C. to about 37° C., and most preferably from about 20° C. to about 27° C., for a period of time preferably of from about one hour to about 24 hours, (overnight as necessary to accommodate processing scheduling of processing staff), preferably from about 6 hours to about 24 hours, and more preferably from about twelve hours to about 18 hours. The extracting solution is preferably pumped at a flow rate of from about 2 mls/min to about 200 mls/min, more preferably from about 5 mls/min to about 100 mls/min and most preferablly from about 30 mls/min to about 60 mls/min. The endonuclease (Benzonase) is optimally active between pH 6 and 10, and from 0° C. to above 42° C. (Merck literature describing product) when provided with 1–2 mM $Mg^{+2}$. Following processing with the extracting solution, the extracting solution is optionally replaced with a hypertonic salt solution prior to replacement of the hypertonic salt solution with water. Under the optional processing procedure, only sufficient water or salt solution need be circulated through the processing vessel to affect one volume change of solution in the processing vessel. Under processing with the various solutions, these solutions are circulated through and/or around the tissue at a temperature of from about 4° C. to about 42° C., preferably from about 20° C. to about 37° C., and most preferably from about 20° C. to about 27° C., for a time period of at least 3 hours, preferably from about 1 to about 24 hours, and most preferably from about 3 to about 6 hours. Following optional processing with the hypertonic salt solution, water for example ultrapure sterile water, or isotonic saline, is circulated through and/or around the tissue and processing vessel such that the available volume of washing solution approximates a 1000-fold dilution of the previous processing solutions. Following the water wash, the tissue is optionally processed with a decontaminating solution.

Throughout processing for all tissue grafts, the tissue is processed at a flow rate sufficient to affect a volume change in the processing vessel about every 30–40 minutes, suitable flow rates including for example of from about 2 mls/min to about 200 mls/min, preferably from about 5 mls/min to about 100 mls/min, more preferably from about 30 mls/min. to about 70 mls/min., even more preferably from about 40 mls/min to about 60 mls/min., and most preferably about 50 mls/min. Following washing with the decontaminating solution, the soft tissue graft may be removed from the processing vessel and transferred into storage solution containing for example, buffered isotonic saline, 70% isopropanol, or 0.0005% to 0.005%, preferably 0.001% chlorine dioxide in sterile ultrapure water/isotonic saline, and packaged in a volume of storage solution sufficient to cover the tissue preventing dehydration.

Alternatively, the storage solutions can be pumped into the processing vessel until the decontaminating solution has been adequately exchanged and the whole processing vessel sealed, sterilized for example using gamma-irradiation, and used as the storage container for distribution. Storage of processed soft tissue grafts should be in a solution which covers the graft and which is contained in a container that will prevent evaporation and fluid loss or concentration of solutes. The solution can be isotonic saline, isotonic saline or ultrapure water containing a preservative such as chlorine dioxide, isopropanol, METHYLPARABIN® (Croda, Inc.), antibiotics, antimicrobials, antimycotic agents, antifungal agents, or ultrapure water, or similar bacteriostatic or bacteriocidal agent which do not biologically alter the matrix components of the soft tissue grafts. Suitable storage solutions are well known to those of ordinary skill in the art to which the present invention applies, and such solutions can be readily selected and employed by those of ordinary skill in the art to which the present invention applies without undue experimentation. The storage containers with solution and soft tissue grafts can be terminally sterilized using methods known in the art including but not limited to, gamma irradiation at doses up to 2.5 Mrads.

The following examples illustrate processing of soft tissue grafts according to the invention.

EXAMPLE 1

Saphenous vein tissues (two) from each leg of an acceptable human donor were carefully dissected under sterile conditions to remove all visible fat deposits and the side vessels were tied off using non-resorbable suture materials such that the ties did not occur in close proximity to the long run of the vessel. Sutures can restrict the devitalization process and the tissues under the sutures were removed following devitalization. For long vein grafts (40–60 cm) (FIG. 1), the distal ends of the veins were cannulated onto the ribbed attachment of the inlet port(s) and single sutures used to secure each vein. Additional suture lines were attached to the proximal ends of the veins. The veins were then removed from the dissecting solution (ultrapure water containing 50 mM Tris-HCl (pH 7.2), 5 mM EDTA, and one or more antibiotics) and transferred to the processing vessel which had been temporarily inverted. The second suture line along with the vein was passed through the processing vessel and secured to a point on the outlet port end of the processing vessel. Prior to closing the processing vessel, a portion of the extracting solution was gently added to the processing vessel and the inlet port, with attached vein, was then secured. The processing vessel was then turned such that the inlet port was down and the outlet port was up and the vessel attached to its support racking system via clamps. Sterile disposable tubing was attached to the inlet port and to pump tubing in a peristaltic pump. Further, sterile disposable tubing was attached to the inflow side of the peristaltic pump and to the solution reservoir which contained all remaining extracting solution. Total extracting solution volume approximated 250 ml. Finally, sterile disposable tubing was attached between the top (outlet) port of the processing vessel and the solution reservoir. Sterile, in-line, filters were added at appropriate positions in the fluid flow to safeguard sterility during processing. The extracting solution was then pumped into, through and out of the processing vessel such that flow of fluids through the luminal part of the vein tubule passed into the processing vessel to affect constant solution change in the processing vessel and out through the outlet port to a solution reservoir. By processing the vein in an inverted state, air which had been "trapped" in the luminal space of the vein was induced to exit facilitating equal access of the processing solutions to the vein tissue being processed. Processing of the vein tissue with the extracting solution was performed at 25±5° C. for 16 hours using a flow rate of the extracting solution of 50 mls/min. The extracting solution consisted of 50 mM Tris HCL (pH 8), 2 mM $MgCl_2$, 1% (w:v) N-lauroyl sarcosinate, and endonuclease (Benzonase, a registered product of EM Industries, Inc.) (41.8 Units/ml). Following processing with the extracting solution, the extracting solution was replaced with a hypertonic salt solution, preferably 0.5M NaCl (250 mls at a pump rate of 50 mls/min.) over a period of one hour. Only sufficient salt solution was circulated through the processing vessel to affect one volume change of solution in the processing vessel. Following processing with the decontaminating solution, the vein was removed from the processing vessel and transferred into storage solution of 0.001% chlorine dioxide in sterile ultrapure water and packaged in a volume of this solution sufficient to cover the tissue. Following processing with the decontaminating solution, the vein was removed from the processing vessel and transferred into storage solution of 0.001% chlorine dioxide in sterile ultrapure water and packaged in a volume of this solution sufficient to cover the tissue. Following devitalization, representative sections of the tissue were removed and fixed in buffered formalin and embedded for preparation of histology slides. When stained using standard hemotoxalin/eosin, Mason's Trichrome, etc., the tissues were found to be devoid of visible cellular remnants, however the medial layer typically stained "pink" (Mason's trichrome stain) indicative of residual cytoplasmic proteins. Innumohistochemical staining of these tissues revealed these pink stained areas to contain residual high molecular weitht cytoplasmic proteins (actins).

EXAMPLE 2

Saphenous vein tissues (two) from each leg of an acceptable human donor were carefully dissected under sterile conditions to remove all visible fat deposits and side vessels were tied off using nonresorbable suture materials such that the ties did not occur in close proximity to the long run of the vessel. Sutures can restrict the decellularization process and the tissues under the sutures were removed following decellularization. For these long vein grafts (33 and 28 cm) (FIG. 1), the distal ends of the veins were cannulated onto the ribbed attachment of the inlet port(s) and single sutures used to secure each vein. Additional suture lines were attached to the proximal ends of the veins. At this point, the veins were removed from the dissecting solution (ultrapure water containing 50 mM Tris-HCl (pH 7.2), 5 mM EDTA, and one or more antibiotics and transferred to the processing vessel which had been temporarily inverted. The second suture line along with the vein was passed through the processing vessel and secured to a point on the outlet port end of the processing vessel. Prior to closing the processing vessel, a portion of the extracting solution was gently added to the processing vessel and the inlet port, with attached vein, was then secured. The processing vessel was then turned such that the inlet port was down and the outlet port was up and the vessel attached to its support racking system via clamps. Sterile disposable tubing was attached to the inlet port and to pump tubing in a peristaltic pump. Further, sterile disposable tubing was attached to the inflow side of the peristaltic pump and to the solution reservoir which contained all remaining first extracting solution. Total processing solution volume approximated 250 ml. Finally, sterile disposable tubing was attached between the top (outlet) port of the processing vessel and the solution reservoir. Sterile, in-line, filters were added at appropriate positions in the fluid flow to safeguard sterility during processing. The extracting solution was pumped into, through and out of the processing vessel such that flow of fluids through the luminal part of the vein tubule passed into the processing vessel to affect constant solution change in the processing vessel and out through the outlet port to a solution reservoir. By processing the vein in an inverted state, air which had been "trapped" in the luminal space of the vein was induced to exit facilitating equal access of the processing solutions to the vein tissue being processed. Processing of the vein tissue with the extracting solution was performed at 25±5° C. for 16 hours using a flow rate of the extracting solution of 50 mls/min. The extracting solution consisted of 50 mM Tris-HCl (pH 7.2), 2 mM $MgCl_2$, 0.1% (w:v) n-lauroyl sarcosinate, and endonuclease (Benzonase, a registered product of EM Industries, Inc.) (41.8 Units/ml). Following processing with the extracting solution, the extracting solution was replaced with a hypertonic salt solution containing 1.0M KCL (50 mls/min. flow rate) through the tissue at room temperature (25±5° C.) for a time period of 3 hours. Following processing with the hypertonic salt solution, ultrapure sterile water was circulated through the tissue and processing vessel such that the available volume of washing solution approximated a 1000-fold dilution of the salt solution with a flow rate of 50 mls/min. for 1.5 hours. Following washing in this final processing step, the vein was removed from the processing vessel and transferred into storage solution of 0.001% chlorine dioxide in sterile ultrapure water and packaged in a volume of this solution sufficient to cover the tissue. Following devitalization, representative sections of the tissue were removed and fixed in buffered formalin and embedded for preparation of histology slides. When stained using standard hemotoxalin/eosin, Mason's Trichrome, etc., the tissues were found to be devoid of visible cellular remnents, however the medial layer typically stained "pink" (Mason's trichrome stain) indicative of residual cytoplasmic proteins. Immunohistochemical staining of these tissues revealed these pink stained areas to contain residual high molecular weight cytoplasmic proteins (actins).

EXAMPLE 3

Internal mammary artery tissues (two) from an acceptable human donor were carefully dissected under sterile conditions to remove all visible fat deposits and side vessels were tied off using nonresorbable suture materials such that the ties did not occur in close proximity to the long run of the vessel. Sutures can restrict the decellularization process and the tissues under the sutures were removed following decellularization. For short artery grafts (11 and 8 cm) (FIG. 1), one end of each artery were cannulated onto the ribbed attachment of the inlet port(s) and single sutures used to secure each arteries. The arteries were then removed from the dissecting solution (ultrapure water containing 50 mM Tris-HCl (pH 7.2), 5 mM EDTA, and one or more antibiotics) and transferred to the processing vessel which had been temporarily inverted. Prior to closing the processing vessel, a portion of the extracting solution was gently added to the processing vessel and the inlet port, with attached artery, was then secured. At this point, the processing vessel was turned such that the inlet port was down and the outlet port was up and the vessel attached to its support racking system via clamps. Sterile disposable tubing was attached to the inlet port and to pump tubing in a peristaltic pump. Further, sterile disposable tubing was attached to the inflow side of the peristaltic pump and to the solution reservoir which contained all remaining extracting solution. Total processing solution volume approximated 150 ml. Finally, sterile disposable tubing was attached between the top (outlet) port of the processing vessel and the solution reservoir. Sterile, in-line, filters were added at appropriate positions in the fluid flow to safeguard sterility during processing. The extracting solution was pumped into, through and out of the processing vessel such that flow of fluids through the luminal part of the artery tubule passed into the processing vessel to affect constant solution change in the processing vessel and out through the outlet port to a solution reservoir. By processing the artery in an inverted state, air which had been "trapped" in the luminal space of the vein was induced to exit facilitating equal access of the processing solutions to the vein tissue being processed. Processing of the artery tissue with the extracting solution was performed at 25±5° C. for 16 hours using a flow rate of the extracting solution of 50 mls/min. The extracting solution consisted of 50 mM Tris-HCl (pH 7.2), 5 mM $MgCl_2$, 0.01% (w:v) N-lauryl sarcosinate, and endonuclease (Benzonase, a registered product of EM Industries, Inc.) (41.8 Units/ml). Following processing with extracting solution, the extracting solution was replaced with a hypertonic salt solution of 0.5 KCL in sterile ultrapure water (250 mls at a pump rate of 60 mls/min.) which was then replaced with ultrapure water buffered with 50 mM Tris-HCl (pH 7.2). Under this processing procedure, only sufficient ultrapure water was circulated through the processing vessel to affect one volume change of solution in the processing vessel. Under the processing with water solution, this water solution was circulated (flow rate of 30 mls/min.) through the tissue at room temperature (25±5° C.), for a time period of 3 hours. Following processing with the second processing solution, ultrapure sterile water was circulated through the tissue and processing vessel such that the available volume of washing solution approximated a 1000-fold dilution of the KCL present in the hypertonic salt solution with a flow rate of 50 ml/min. for 1.5 hours. Following washing in this final processing step, the artery was removed from the processing vessel and transferred into storage solution of 70% (v:v) pharmaceutical grade isopropanol in sterile ultrapure water and packaged in a volume of this solution sufficient to cover the tissue. Following devitalization, representative sections of the tissue were removed and fixed in buffered formalin and embedded for preparation of histology slides. When stained using standard hemotoxalin/eosin, Mason's Trichrome, etc., the tissues were found to be devoid of visible cellular remnents, however the medial layer typically stained "pink" (Mason's trichrome stain) indicative of residual cytoplasmic porteins. Immunohistochemical staining of these tissues revealed these pink staind areas to contain residual high molecular weight cytoplasmic proteins (actins).

EXAMPLE 4

Aortic and pulmonary tissues (one each) from a heart of an acceptable human donor were carefully dissected under sterile conditions to remove all visible fat deposits and cardiac muscle tissue (leaving only a small but visible band of cardiac muscle tissue around the proximal end of the conduit. The valves were then removed from the dissecting solution (ultrapure water containing 50 mM Tris-HCl (pH 7.2), 5 mM EDTA, and one or more antibiotics) and transferred to the deformable (plastic) processing vessel (FIG. 2). Prior to closing the processing vessel, a portion of the extracting solution was gently added to the processing vessel and the side access port closed using the clamping mechanism illustrated in FIG. 2. The proximal end of the heart valve(s) was placed towards the inlet port and the distal end(s) of the valve was placed towards the outlet port. At this point, the processing vessel was placed such that the inlet port was down and the outlet port was up and the vessel attached to its support racking system via clamps. Sterile disposable tubing was attached to the inlet port and to pump tubing in a peristaltic pump. Further, sterile disposable tubing was attached to the inflow side of the peristaltic pump and to the solution reservoir which contained all remaining extracting solution. Total processing solution volume approximated 350 ml. Finally, sterile disposable tubing was attached between the top (outlet) port of the processing vessel and the solution reservoir. Sterile, in-line, filters were added at appropriate positions in the fluid flow to safeguard sterility during processing. The extracting solution was pumped into, through and out of the processing vessel such that flow of fluids through the luminal part of the heart valve tubule passed into the processing vessel to affect constant solution change in the processing vessel and out through the outlet port to a solution reservoir. By processing the heart valve in a noninverted state, air which had been "trapped" in the luminal spaces behind the leaflets of the heart valve was induced to exit facilitating equal access of the processing solutions to the heart valve tissue being processed. Processing of the valve and conduit tissue with the extracting solution was performed at 25±5° C. for 16 hours using a flow rate of the extracting solution of 50 mls/min.. The extracting solution consisted of 50 mM Tris-HCl (pH 7.2), 2 mM $MgCl_2$, 1% (w:v) N-lauroylsarcosinate, and endonuclease (Benzonase, a registered product of EM Industries, Inc.) (41.8 Units/ml). Following processing with the extracting solution, the extracting solution was replaced with sterile ultrapure water (350 mls at a pump rate of 50 mls/min. being recirculated over a time period of 3 hours). Under this processing procedure, only sufficient ultrapure water was circulated through the processing vessel to affect one volume change of solution in the processing vessel. When optionally processing with salt solution, the hypertonic salt solution is circulated (flow rate of 30 mls/min.) through the tissue at room temperature (25±5° C.), for a time period of 5 hours. Following washing in this final processing step, the heart valve(s) was (were) removed from the processing vessel and transferred into storage solution of 0.05% chlorine dioxide in sterile ultrapure water and packaged in a volume of this solution sufficient to cover the tissue. Following devitalization, representative sections of the tissue were removed and fixed in buffered formalin and embedded for preparation of histology slides. When stained using standard hemotoxalin/eosin, Mason's Trichrome, etc., the tissues were found to be devoid of visible cellular remnants, however the medial layer typically stained "pink" (Mason's trichrome stain) indicative of residual cytoplasmic porteins. Immunohistochemical staining of these tissues revealed these pink staind areas to contain residual high molecular weight cytoplasmic proteins (actins).

EXAMPLE 5

In this example, artery tissues were processed according to the procedure described by Klement and Brendel (U.S. Pat. No. 4,776,853) using gentle aggitation in closed vessels. The tissues were treated for 18 hours in a slightly alkaline buffered solution containing the chelating agent EDTA. The tissues were then incubated, again in a closed container, in a solution of 1% Triton X-100 containing DNase and RNase at the quantities and volumes described for 48 hours. The tissues were then incubated, again in a closed container, in a hypotonic solution of 1% sodium laurylsulfate (SDS) for 72 hours at the volumes described by Klement and Brendel. Following these steps, the tissues were incubated in a hypertonic salt solution using the volumes and time described and then transferred to isotonic saline to remove the hypertonic salt solutions. Following decellularization, representative sections of the tissue were removed and fixed in buffered formalin and embedded for preparation of histology slides. When stained using standard hemotoxalin/eosin, Mason's Trichrome, etc., the tissues were found to be devoid of visible cellular remnants and the medial layer did not stain "pink" (Mason's trichrome stain) indicative of an absence of residual cytoplasmic proteins. Immunohistochemical staining of these tissues revealed an absence of residual high molecular weight cytoplasmic proteins (actins) conforming to the specifications of Klement and Brendel in the production of a totally decellularized, as per their specification, tissue.

While the invention has been described in connection with specific embodiments thereof, it will be understood that it is capable of further modifications and this application is intended to cover any variations, uses, or adaptations of the invention following, in general, the principles of the invention and including such departures from the present disclosure as come hypotonic buffered within known or customary practice within the art to which the invention pertains and as may be applied to the essential features hereinbefore set forth as follows in the scope of the appended claims. Any references including patents cited herein are incorporated herein in their entirety.

What is claimed:

1. A process for preparing an devitalized soft tissue graft for implantation into a mammalian system, comprising:
   extracting a soft tissue sample with an extracting solution comprising one or more non-denaturing detergents, said non-denaturing detergents including n-lauroyl sarcosinate, to produce an extracted tissue;
   washing said extracted tissue with a decontaminating water solution comprising one or more decontaminating agents to produce said devitalized soft tissue graft; and
   storing said devitalized soft tissue graft in a storage solution; said devitalized soft tissue graft is essentially free from metabolically viable and/or reproductively viable cells, and retains non-viable cells and/or cellular elements.

2. A process for preparing an devitalized soft tissue graft for implantation into a mammalian system, comprising:
   inducing a pressure mediated flow of an extracting solution comprising one or more non-denaturing detergents, said non-denaturing detergents including n-lauroyl sarcosinate, through soft tissue, to produce extracted tissue;
   washing said extracted tissue comprising inducing a pressure mediated flow of a decontaminating water solution comprising one or more decontaminating agents, through said extracted tissue, to produce said devitalized soft tissue graft; and
   storing said devitalized soft tissue graft in a storage solution, said devitalized soft tissue graft is essentially free from metabolically viable and/or reproductively viable cells, and retains non-viable cells and/or cellular elements.

3. The process of claim 1 or 2, wherein said process does not comprise a denaturing detergent.

4. The process of claim 1 or 2, further comprising prior to said step of washing, first washing said extracted tissue with water.

5. The process of claim 1 or 2, wherein said extracting solution comprises one or more endonucleases.

6. The process of claim 5, wherein said one or more endonucleases comprise one or more broad spectrum endonucleases capable of degrading both deoxyribonucleic acids and ribonucleic acids.

7. The process of claim 6, wherein said one or more broad-spectrum endonucleases comprise one or more recombinant endonucleases.

8. The process of claim 7, wherein said one or more recombinant endonucleases comprise Serratia marcescens nuclease.

9. The process of claim 5, wherein said one or more endonucleases are present in said extracting solution at a concentration sufficient to degrade nucleic acids present in said tissue sample.

10. The process of claim 9, wherein said one or more endonucleases are present in said extracting solution at a concentration of from about 20 U/ml tissue to about 400 U/ml tissue.

11. The process of claim 10, wherein said one or more endonucleases are present in said extracting solution at a concentration of about 50 U/ml tissue.

12. The process of claim 1 or 2, wherein said extracting solution is a hypotonic buffered solution at an alkaline pH.

13. The process of claim 1 or 2, wherein said extracting solution is recirculated through said soft tissue graft.

14. The process of claim 1 or 2, wherein said decontaminating water solution is recirculated through said soft tissue graft.

15. The process of claim 4, wherein said water solution is recirculated through said soft tissue graft.

16. The process of claim 1, further comprising treating said tissue with a hypotonic salt solution.

17. The process of claim 1, further comprising treating said tissue with a hypertonic salt solution.

18. The process of claim 2, further comprising inducing a pressure mediated flow of a hypotonic salt solution through said extracted tissue.

19. The process of claim 2, further comprising inducing a pressure mediated flow of a hypertonic salt solution through said extracted tissue.

20. The process of claim 1 or 2, wherein said devitalized soft tissue graft retains non-viable cells and/or cytoplasmic elements.

21. The process of claim 10, wherein said one or more endonucleases are present in said extracting solution at a concentration of about 400 U/ml tissue.

22. The process of claim 16 or 17, wherein said hypotonic salt solution is recirculated through said soft tissue graft.

23. The process of claim 16 or 17, wherein said hypertonic salt solution is recirculated through said soft tissue graft.

24. The process of claim 1 or 2, wherein said decontaminating water solution comprises USP sterile endotoxin free water.

25. The process of claim 24, wherein said decontaminating water solution further comprises one or more decontaminating agents selected from the group consisting of an antimicrobial agent, an alcohol, chlorine dioxide, and an antibiotic.

26. The process of claim 1 or 2, wherein said storage solution comprises one or more decontaminating agents.

27. The process of claim 26, wherein said one or more decontaminating agents are selected from the group consisting of an antimicrobial agent, an alcohol, chlorine dioxide, ethanol, isopropanol, methanol, glycerol, methylparaben, and an antibiotic.

28. The process of claim 25, wherein said decontaminating agents are non-reactive towards said one or more non-denaturing detergents and the tissue.

29. The process of claim 1 or 2, wherein said storage solution comprises USP sterile, endotoxin-free, water.

30. The process of claim 27, wherein said chlorine dioxide or said methylparaben are present at a concentration in the range of from 0.001% to 0.1% (v:v).

31. The process of claim 27, wherein said ethanol, isopropanol, methanol, or glycerol are present at a concentration in the range of from 20% to 90% (v:v).

32. The process of claim 1 or 2, wherein said extracting solution has an alkaline pH.

33. The process of claim 32, wherein said extracting solution further comprises one or more organic or inorganic buffers, wherein an alkaline pH is maintained, and an osmolality of the extracting solution which is hypotonic to the cells in said soft tissue is maintained.

34. The process of claim 1 or 2, wherein said non-denaturing detergents comprise one or more detergents selected from the group consisting of a polyoxyethylene alcohol, a polyoxyethylene isoalcohol, a polyoxyethylene p-t-octyl phenol, a polyoxyethylene nonyphenol, a polyoxyethylene ester of a fatty acid, and a polyoxyethylene sorbitol ester.

35. The process of claim 34, wherein said one or more non-denaturing detergents are present in said extracting solution at a concentration of from about 0.001% (w:v) to about 10% (w:v).

36. The process of claim 35, wherein said one or more non-denaturing detergents are present in said extracting solution at a concentration of from about 0.01% (w:v) to about 5% (w:v).

37. The process of claim 36, wherein said one or more non-denaturing detergents are present in said extracting solution at a concentration of from about 0.1% (w:v) to about 2.0% (w:v).

38. The process of claim 4, wherein said extracted tissue is washed with a volume of one or more of said water, a hypotonic salt solution, a hypertonic salt solution, and said decontaminating solution, sufficient to cause an approximate 1:1000 dilution of a concentration of said extracting solution.

39. The process of claim 1 or 2, wherein said step of extracting is carried out for a period of time of from about 6 hours to about 24 hours.

40. The process of claim 39, wherein said step of extracting is carried out for a period of time of from about 12 hours to about 18 hours.

41. The process of claim 1 or 2, wherein said extracting solution further comprises one or more decontaminating agents.

42. The process of claim 17 or 19, wherein said hypertonic salt solution comprises water solutions comprising one or more members selected from the group consisting of a monovalent salt, a divalent salt, and an antimicrobial agent.

43. The process of claim 2, wherein any one or more of said steps of inducing and washing are carried out at a flow rate sufficient to carry away solutes dissolved in said extracting solution.

44. The process of claim 43, wherein said flow rate is from about 2 mls/minute to about 200 mls/minute.

45. The process of claim 44, wherein said flow rate is from about 5 mls/minute to about 100 mls/minute.

46. The process of claim 45, wherein said flow rate is from about 30 mls/minute to about 60 mls/minute.

47. The process of claim 42, wherein said salt solution comprises one or more members selected from the group consisting of sodium hydroxide, sodium phosphate, potassium sulfate, lithium sulfate, calcium phosphate, potassium phosphate, lithium phosphate, ammonium chloride, magnesium chloride, calcium sulfate, calcium chloride, calcium hydroxide, magnesium chloride, lithium chloride, potassium chloride, and sodium chloride.

48. The process of claim 47, wherein said monovalent salt and said divalent salt are present in said hypertonic salt solution at a concentration of from about 0.00001 M to about 2.0 M.

49. The process of claim 48, wherein said concentration is from about 0.0001 to about 0.5 M.

50. The process of claim 49, herein said concentration is from about 0.0002 to about 0.08 M.

51. The process of claim 1, wherein said step of extracting is carried out for a time period of from about 6 hours to about 24 hours.

52. The process of claim 2, wherein said step of inducing is carried out for a time period of from about 6 hours to about 24 hours.

53. The process of claim 51 or 52, wherein said time period is from about 12 to about 16 hours.

54. The process of claim 1, wherein said step of extracting is carried out at a temperature of from about 4° C. to about 42° C.

55. The process of claim 2, wherein said step of inducing is carried out at a temperature of from about 4° C. to about 42° C.

56. The process of claim 54 or 55, wherein said temperature is from about 20° C. to about 27° C.

57. The process of claim 16, wherein said step of treating said tissue with a hypotonic salt solution is carried out for a time period of at least 3 hours.

58. The process of claim 18, wherein said step of inducing a pressure mediated flow of a hypotonic salt solution through said extracted tissue is carried out for a time period of at least 3 hours.

59. The process of claim 17, wherein said step of treating said tissue with a hypertonic salt solution is carried out for a time period of at least 3 hours.

60. The process of claim 19, wherein said step of inducing a pressure mediated flow of a hypertonic salt solution through said extracted tissue is carried out for a time period of at least 3 hours.

61. The process of claim 16, wherein said step of treating said tissue with a hypotonic salt solution is carried out at a temperature of from about 0° C. to about 42° C.

62. The process of claim 18, wherein said step of inducing a pressure mediated flow of a hypotonic salt solution through said extracted tissue is carried out at a temperature of from about 0° C. to about 42° C.

63. The process of claim 17, wherein said step of treating said tissue with a hypertonic salt solution is carried out at a temperature of from about 0° C. to about 42° C.

64. The process of claim 19, wherein said step of inducing a pressure mediated flow of a hypertonic salt solution through said extracted tissue is carried out at a temperature of from about 0° C. to about 42° C.

65. The process of claim 62, 63, or 64, wherein said temperature is from about 20° C. to about 27° C.

* * * * *